US011961591B2

(12) United States Patent
Kaznadzey

(10) Patent No.: US 11,961,591 B2
(45) Date of Patent: Apr. 16, 2024

(54) METHODS, SYSTEMS, AND COMPUTER-READABLE MEDIA FOR TANDEM DUPLICATION DETECTION

(71) Applicant: LIFE TECHNOLOGIES CORPORATION, Carlsbad, CA (US)

(72) Inventor: Denis Kaznadzey, Walnut Creek, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1003 days.

(21) Appl. No.: 16/206,003

(22) Filed: Nov. 30, 2018

(65) Prior Publication Data

US 2019/0172554 A1 Jun. 6, 2019

Related U.S. Application Data

(60) Provisional application No. 62/598,053, filed on Dec. 13, 2017, provisional application No. 62/593,547, filed on Dec. 1, 2017.

(51) Int. Cl.
*G16B 30/00* (2019.01)
*C12Q 1/6869* (2018.01)
*C12Q 1/6886* (2018.01)

(52) U.S. Cl.
CPC ........... *G16B 30/00* (2019.02); *C12Q 1/6869* (2013.01); *C12Q 1/6886* (2013.01); *C12Q 2600/156* (2013.01); *C12Q 2600/158* (2013.01)

(58) Field of Classification Search
CPC ..... G16B 30/00; C12Q 1/6886; C12Q 1/6869

(Continued)

(56) References Cited

U.S. PATENT DOCUMENTS

2016/0098517 A1 4/2016 Park et al.

FOREIGN PATENT DOCUMENTS

CN 103103251 A 5/2013
CN 106062214 A 10/2016

(Continued)

OTHER PUBLICATIONS

Shimizu K, Tsuda K., SlideSort: all pairs similarity search for short reads. Bioinformatics. Feb. 15, 2011;27(4):464-70. Epub Dec. 9, 2010. (Year: 2011).*

(Continued)

*Primary Examiner* — Russell S Negin
*Assistant Examiner* — Guozhen Liu
(74) *Attorney, Agent, or Firm* — Carolyn Koenig

(57) ABSTRACT

A method for detecting a tandem duplication in an FLT3 gene of a sample, includes mapping reads corresponding to targeted regions of exons of the FLT3 gene to a reference sequence. A partially mapped read includes a mapped portion, a soft-clipped portion and a breakpoint. Analyzing the partially mapped reads intersecting a column of the pileup includes detecting a duplication in the soft-clipped portion by comparing the soft-clipped portion to the mapped portion adjacent to the breakpoint; determining an insert size of the duplication in the soft-clipped portion; and assigning the partially mapped read to a category based on the insert size. Categories correspond to insert sizes. The categories are filtered and converted into features corresponding to the column. The features corresponding to one or more columns representing a same insert are merged to determine a location and size of a tandem duplication.

20 Claims, 5 Drawing Sheets

(58) Field of Classification Search
USPC .......................................................... 702/19
See application file for complete search history.

(56) References Cited

FOREIGN PATENT DOCUMENTS

| CN | 107002123 A | 8/2017 |
|---|---|---|
| WO | WO-2015112619 A1 | 7/2015 |

OTHER PUBLICATIONS

Kai Ye, Jiayin Wang et al. : Systematic discovery of complex insertions and deletions in human cancers, Nature Medicine vol. 22, No. 1, Jan. 2016 (Year: 2016).*

Boyer et al., "A Fast String Searching Algorithm" Communications of the ACM, vol. 20, No. 10, 1977, pp. 762-772.

International Search Report and Written Opinion for Application No. PCT/US2018/063323, dated Feb. 19, 2019, 15 pages.

Rustagi N., et al., "ITD assembler: an algorithm for internal tandem duplication discovery from short-read sequencing data", BMC Bioinformatics, vol. 17, No. 1, Apr. 27, 2016 (Apr. 27, 2016), XP055552575, DOI: 10.1186/s12859-016-1031-8.

Spencer D.H., et al., "Detection of FLT3 Internal Tandem Duplication in Targeted, Short-Read-Length, Next-Generation Sequencing Data", The Journal of Molecular Diagnostics, vol. 15, No. 1, Jan. 1, 2013 (Jan. 1, 2013), pp. 81-93, XP055551710, US, ISSN: 1525-1578, DOI: 10.1016/j.jmoldx.2012.08.001.

Wang J., et al.: "CREST maps somatic structural variation in cancer genomes with base-pair resolution", Nature Methods, vol. 8, No. 8, Aug. 1, 2011 (Aug. 1, 2011), pp. 652-654, XP055551512, New York, ISSN: 1548-7091, DOI: 10.1038/nmeth.1628.

Ye K., et al., "Pindel: a pattern growth approach to detect break points of large deletions and medium sized insertions from paired-end short reads", Bioinformatics, Nov. 1, 2009 (Nov. 1, 2009), pp. 2865-2871, XP055367945, England, DOI: 10.1093/bioinformatics/btp394, Retrieved from the Internet:URL:https://academic.oup.com/bioinformatics/article-pdf/25/21/2865/6059071/btp394.pdf.

* cited by examiner

METHODS, SYSTEMS, AND COMPUTER-READABLE MEDIA FOR TANDEM DUPLICATION DETECTION

CROSS-REFERENCE

This application claims the benefit under 35 U.S.C. § 119(e) of U.S. Provisional Application No. 62/593,547, filed Dec. 1, 2017 and U.S. Provisional Application No. 62/598,053, filed Dec. 13, 2017. The entire contents of the aforementioned applications are incorporated by reference herein.

FIELD

This application generally relates to methods, systems, and computer-readable media for detection of tandem duplication, and, more specifically, to methods, systems, and computer-readable media for detection of tandem duplication based on or using nucleic acid sequencing data and next-generation sequencing technology or systems.

BACKGROUND

Nucleic acid sequencing data may be obtained in various ways, including using next-generation sequencing systems such as, for example, the Ion PGM™, Ion Proton™, and Ion S5™ systems implementing Ion Torrent™ sequencing technology (see, e.g., U.S. Pat. No. 7,948,015, issued May 24, 2011, U.S. Pat. Appl. Publ. No. 2010/0137143, published Jun. 3, 2010, U.S. Pat. Appl. Publ. No. 2009/0026082, published Jan. 29, 2009, and U.S. Pat. Appl. Publ. No. 2010/0282617, published Nov. 11, 2010, which are all incorporated by reference herein in their entirety). Such next-generation sequencing systems may be used in conjunction with primers for targets of interest, which primers may be designed or prepared in various ways, including as described in U.S. Pat. Appl. Publ. No. 2012/0295819, published Nov. 22, 2012, which is incorporated by reference herein in its entirety. Various aspects of FLT3 mutations have been discussed, including in Pawar et al., "Recent advances and novel agents for FLT3 mutated acute myeloid leukemia," Stem Cell Investigation 1:7 (Mar. 18, 2014) (DOI: 10.3978/j.issn.2306-9759.2014.03.03). There is a need for new and improved methods, systems, and computer-readable media for better and more accurate detection of tandem duplication.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

SUMMARY

Figure 1:
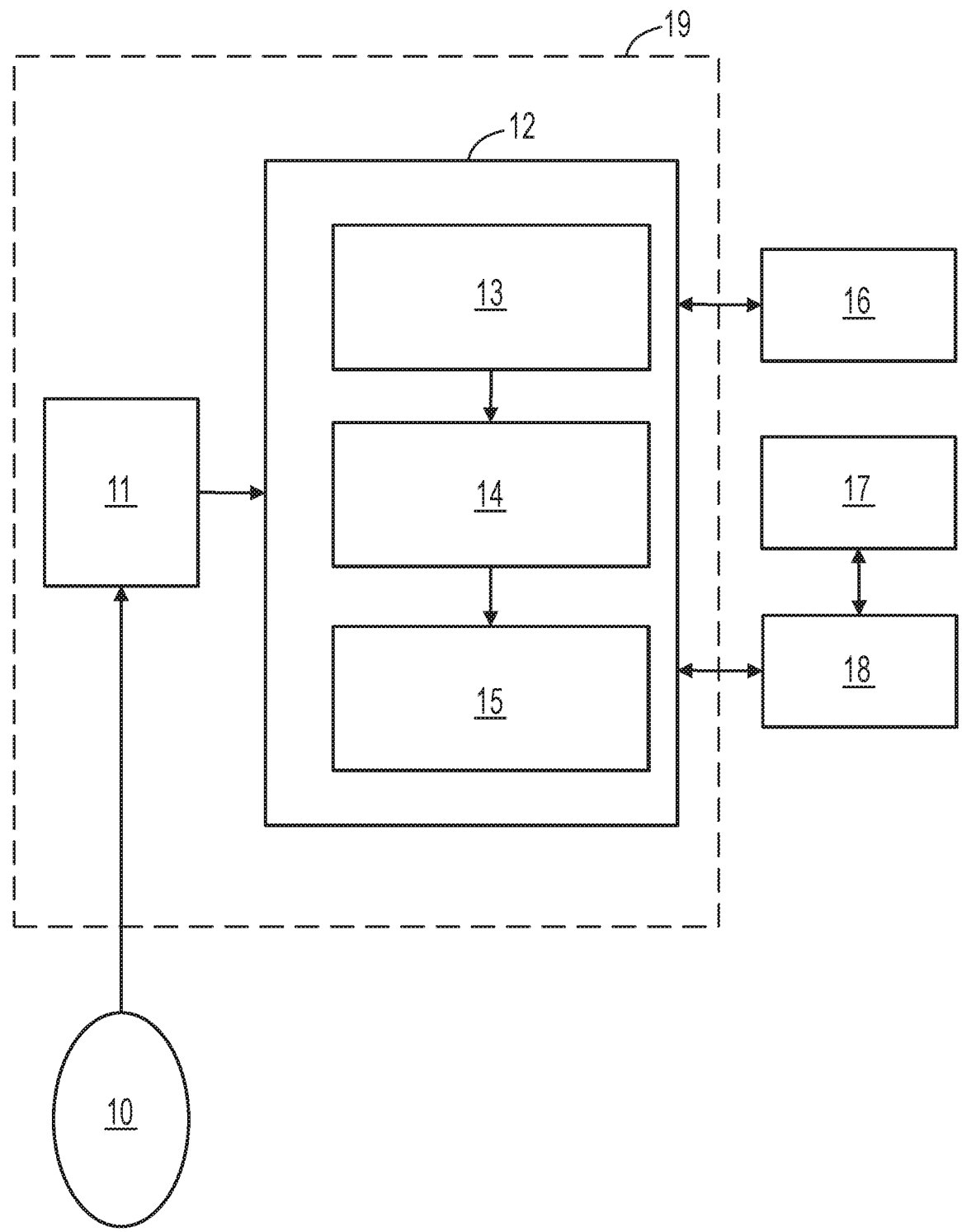
FIG. 1 illustrates an exemplary system for tandem duplication detection using nucleic acid sequencing and/or analysis.

According to various exemplary embodiments, there are provided various methods for detecting tandem duplication as well as various related systems and computer-readable media for detection tandem duplication, including detection of genomic regions or mutations informative of FLT3 status, as further described below.

According to an exemplary embodiment, there is provided a method for detecting an internal tandem duplication in an FLT3 gene of a sample, comprising: (a) amplifying a nucleic acid sample in the presence of a primer pool to produce a plurality of amplicons, the primer pool including a plurality of target specific primers targeting regions of exons of the FLT3 gene; (b) sequencing the amplicons to generate a plurality of reads; (c) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (d) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (e) converting the categories into features corresponding to the column, wherein a feature includes the insert size and a sequence of an insert at an insert position; and (f) merging the features corresponding to one or more columns representing a same insert to determine a location and a size of a tandem duplication.

According to an exemplary embodiment, there is provided a system for detecting an internal tandem duplication in an FLT3 gene of a sample, comprising a machine-readable memory and a processor configured to execute machine-readable instructions, which, when executed by the processor, cause the system to perform a method, comprising: (a) receiving a plurality of reads, wherein the plurality of reads correspond to a plurality of targeted regions of exons of the FLT3 gene; (b) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (c) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (d) converting the categories into features corresponding to the column, wherein a feature includes the insert size and a sequence of an insert at an insert position; and (e) merging the features corresponding to one or more columns representing a same insert to determine a location and a size of a tandem duplication.

According to an exemplary embodiment, there is provided a computer-readable media comprising machine-readable instructions that, when loaded in a machine-readable memory and executed by a processor, are configured to cause a system to perform a method for detecting an internal tandem duplication in an FLT3 gene of a sample, comprising: (a) receiving a plurality of reads, wherein the plurality of reads correspond to a plurality of targeted regions of exons of the FLT3 gene; (b) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (c) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (d) converting the categories into features corresponding to the column, wherein a feature includes the insert size and a sequence of an insert at an insert position; and (e) merging the features corresponding to one or more columns representing a same insert to determine a location and a size of a tandem duplication.

Exemplary Embodiments

The following description and the various embodiments described herein are exemplary and explanatory only and are not to be construed as limiting or restrictive in any way. Other embodiments, features, objects, and advantages of the present teachings will be apparent from the description that follows.

According to various exemplary embodiments, there are provided methods, systems, and computer-readable media for detection of tandem duplication, including detection of genomic regions or mutations informative of FLT3 status. An internal tandem duplication in the FLT3 gene is referred to as FLT3-ITD.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization.

In various embodiments, target nucleic acids generated by the amplification of multiple target-specific sequences from a population of nucleic acid molecules can be sequenced. In some embodiments, the amplification can include hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the amplified target sequences can be ligated to one or more adapters. In some embodiments, the adapters can include one or more nucleotide barcodes or tagging sequences. In some embodiments, the amplified target sequences once ligated to an adapter can undergo a nick translation reaction and/or further amplification to generate a library of adapter-ligated amplified target sequences. Exemplary methods of multiplex amplification are described in U.S. Patent Application Publication No. 2012/0295819, published Nov. 22, 2012, incorporated by reference herein in its entirety.

In various embodiments, the method of performing multiplex PCR amplification includes contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

A plurality of defined spaces or reaction confinement regions may be arranged in an array, and each defined space or reaction confinement regions may be in electrical communication with at least one sensor to allow detection or measurement of one or more detectable or measurable parameter or characteristics. This array is referred to herein as a sensor array. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal.

In some embodiments, a sample may be prepared for detection of internal tandem duplications in the FLT3 gene by multiplex amplification of template polynucleotide strands obtained from the sample. The multiplex amplification may use a set of primers targeting regions of exons of the FLT3 gene. FLT3-ITDs may occur in exons 14 and 15 of the gene.

FIG. 1 illustrates an exemplary system for detection of tandem duplication using nucleic acid sequencing and/or analysis. The system includes an apparatus or sub-system for nucleic acid sequencing and/or analysis 11, a computing server/node/device 12 including a base calling engine 13, a variant calling engine 14, and a tandem duplication detection engine 15, and a display 16, which may be internal and/or external. The apparatus or sub-system for nucleic acid sequencing and/or analysis 11 may be any type of instrument that can generate nucleic acid sequence data from nucleic acid samples, which may include a nucleic acid sequencing instrument, a real-time/digital/quantitative PCR instrument, a microarray scanner, etc. The nucleic acid samples may include nucleic acid samples known to be normal samples or known to be tumor samples. The computing server/node/device 12 may be a workstation, mainframe computer, distributed computing node (part of a "cloud computing" or distributed networking system), personal computer, mobile device, etc. The base calling engine 13 may be any suitable base caller and may be configured to include various signal/data processing modules that may be configured to receive signal/data from the apparatus or sub-system for nucleic acid sequencing and/or analysis 11 to determine base calls and the sequences of sequencing reads for some or the entirety of a sequencing data set. In an embodiment, the base calling engine 13 may be a base caller implemented in Torrent Suite Software (Thermo Fisher Scientific Inc.). In an embodiment, the base calling engine 13 may implement one or more features described in U.S. Pat. Appl. Publ. No. 2012/0109598, published May 3, 2012, and/or U.S. Pat. Appl. Publ. No. 2013/0060482, published Mar. 7, 2013, which are all incorporated by reference herein in their entirety. The base calling engine 13 may also include a mapping or alignment module for mapping or aligning reads to a reference sequence or genome, which may be a whole/partial genome, whole/partial exome, etc. In an embodiment, the mapping or alignment module may include any suitable aligner, including the Torrent Mapping Alignment Program (TMAP), for example. The exemplary system may also include a client device terminal 17, which may include a data analysis API or module and may be communicatively connected to the computing server/node/device 12 via a network connection 18 that may be a "hardwired" physical network connection (e.g., Internet, LAN, WAN, VPN, etc.) or a wireless network connection (e.g., Wi-Fi, WLAN, etc.). The variant calling engine 14 may be configured to include various signal/data processing modules that may be configured to make variant calls and apply post-processing to variant calls, which may include annotating various variant calls and/or features, converting data from flow space to base space, filtering variants, and formatting the variant data for display or use by client device terminal 17. Variant calls may be made using any suitable variant caller. In an embodiment, the variant caller may be Torrent Variant Caller (Thermo Fisher Scientific Inc.). In an embodiment, the apparatus or sub-system for nucleic acid sequencing and/or analysis 11 and the computing server/node/device 12 may be integrated into a single instrument or system comprising components present in a single enclosure 19. The client device terminal 17 may be configured to communicate information to and/or control the operation of the computing server/node/device 12 and its modules and/or operating parameters. In an embodiment, the system 19 may be used with a sample 10 prepared using compositions or kits including one or more primers for tandem duplication detection and/or FLT3 detection. The tandem duplication detection engine 15 may implement one or more of the methods further described herein.

Figure 2:
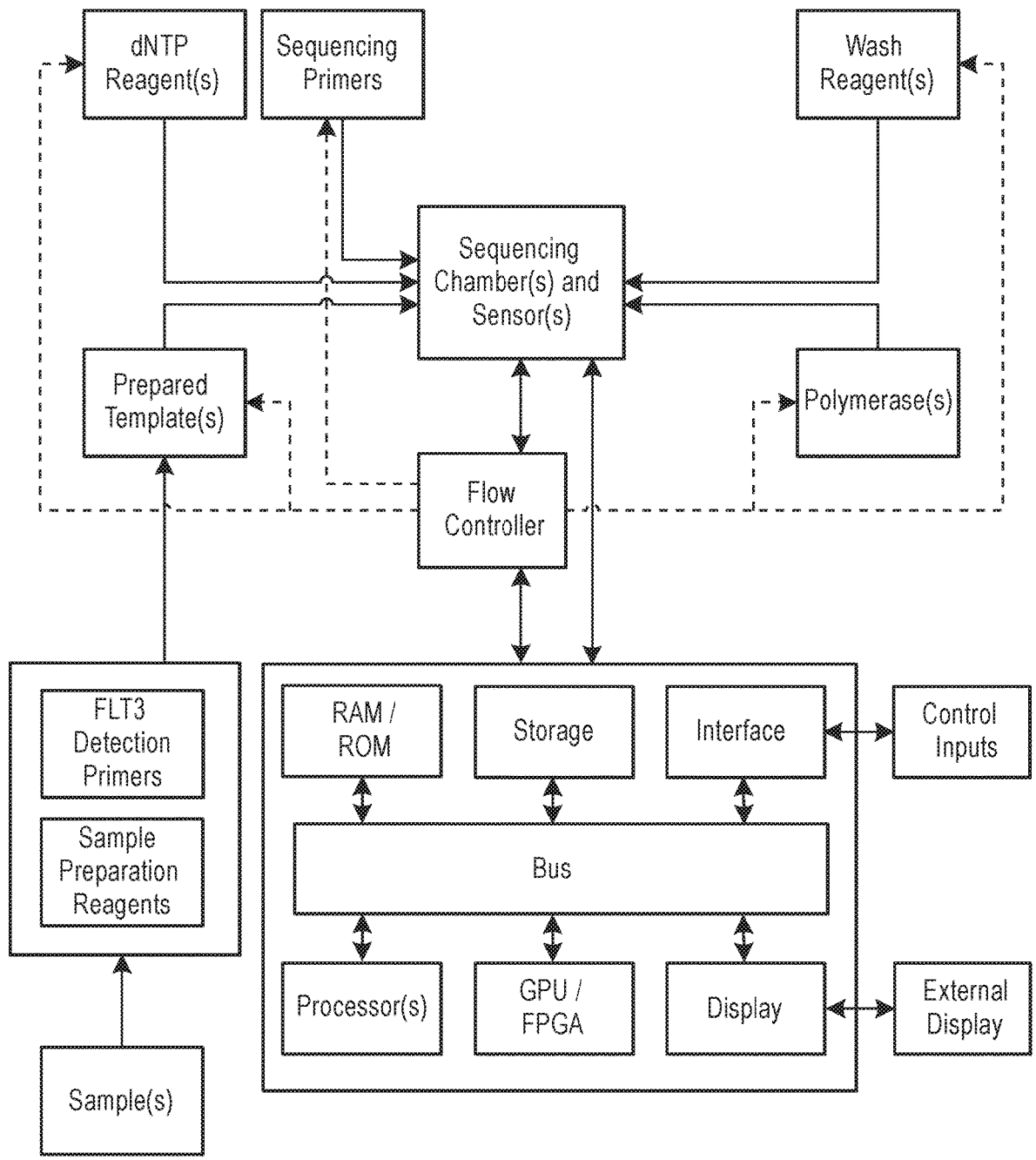
FIG. 2 illustrates an exemplary system for tandem duplication using nucleic acid sequencing and/or analysis.

FIG. 2 illustrates an exemplary system for detection of tandem duplication using nucleic acid sequencing and/or analysis. The system includes an apparatus or sub-system for nucleic acid sequencing and/or analysis, which includes one or more sequencing chambers and sensors, and a flow controller, which is configured to control flow of various reagents, including dNPT reagent(s), sequencing primers, polymerase(s), wash reagents, and prepared templates to the one or more sequencing chambers and sensors. The system also include a computing server/node/device, which includes RAM/ROM, storage, an interface, processor(s), and GPU/FPGA, all of which connected to a bus, and which is connected to control inputs and an display, which may be internal and/or external. The system can be used with one or more samples that may be prepared using a kit including sample preparation reagents and FLT3 detection primers to obtain prepared templates. The computing server/node/device may be programmed to perform a base calling process, a variant calling process, and a tandem duplication detection process. The samples may include nucleic acid samples known to be normal samples or known to be tumor samples. The computing server/node/device may be a workstation, mainframe computer, distributed computing node (part of a "cloud computing" or distributed networking system), personal computer, mobile device, etc. The base calling process may be any suitable base caller and may be configured to determine base calls and the sequences of sequencing reads for some or the entirety of a sequencing data set. In an embodiment, the base calling process may be a base caller implemented in Torrent Suite Software (Thermo Fisher Scientific Inc.). In an embodiment, the base calling process may implement one or more features described in U.S. Pat. Appl. Publ. No. 2012/0109598, published May 3, 2012, and/or U.S. Pat. Appl. Publ. No. 2013/0060482, published Mar. 7, 2013, which are all incorporated by reference herein in their entirety. The base calling process may also include a mapping or alignment process for mapping or aligning reads to a reference sequence or genome, which may be a whole/partial genome, whole/partial exome, etc. In an embodiment, the mapping or alignment process may include any suitable aligner, including the Torrent Mapping Alignment Program (TMAP), for example. The control inputs may be communicatively connected to the computing server/node/device via a network connection that may be a "hardwired" physical network connection (e.g., Internet, LAN, WAN, VPN, etc.) or a wireless network connection (e.g., Wi-Fi, WLAN, etc.). The variant calling process may be configured to include various signal/data processing processes that may be configured to make variant calls and apply post-processing to variant calls, which may include annotating various variant calls and/or features, converting data from flow space to base space, filtering variants, and formatting the variant data. Variant calls may be made using any suitable variant caller. In an embodiment, the variant caller may be Torrent Variant Caller (Thermo Fisher Scientific Inc.). In an embodiment, the apparatus or sub-system for nucleic acid sequencing and/or analysis and the computing server/node/device may be integrated into a single instrument or system comprising components present in a single enclosure. The tandem duplication detection process may implement one or more of the methods further described herein.

Figure 3:
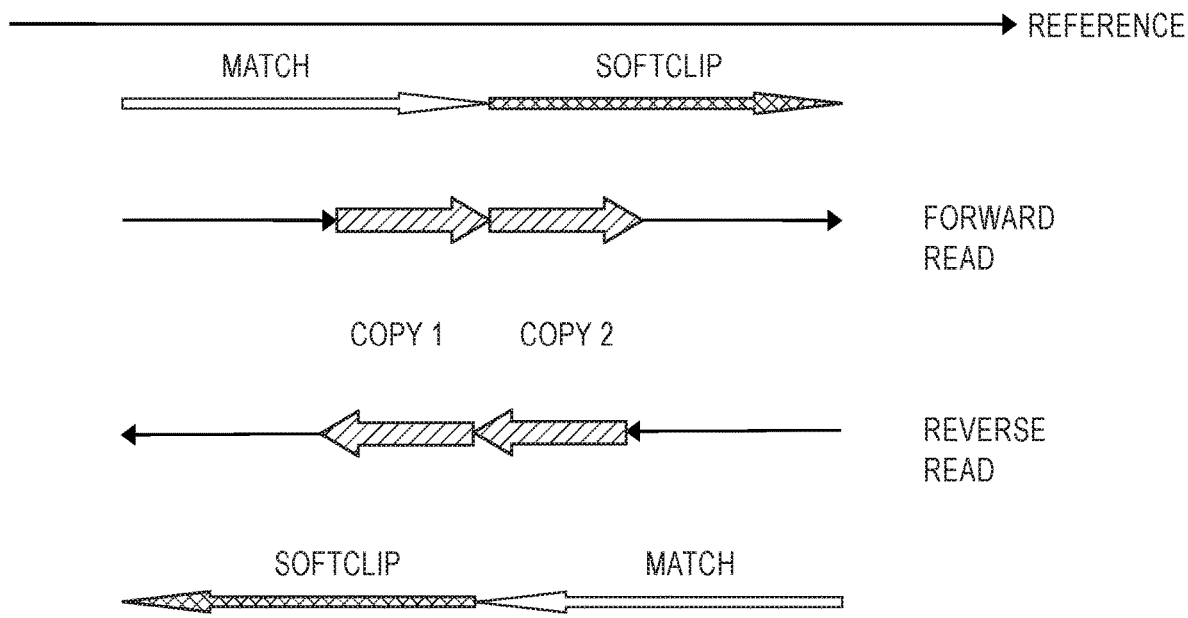
FIG. 3 illustrates examples of partially mapped reads.

In some embodiments, the variant caller in a standard pipeline may detect an insert that includes multiple base-pairs. However, the presence of long inserts (e.g., 10 base-pairs or over) often results in partial alignment of the reads, in which the insert itself and the downstream reference match get excluded from alignment (which is sometimes also referred to as soft-clipped). The reads with inserts located close to the 3' end are particularly affected. The soft-clipped parts are not processed by the standard pipeline, so inserts in soft-clipped parts are not detected. One reason for lack of detection of long inserts is that the mapping or alignment process may only partially map reads with longer inserts and softclip the unmapped portion of the read. FIG. 3 illustrates examples of partially mapped reads. FIG. 3 shows "copy 1" and "copy 2" of tandem duplications present in a forward read and a reverse read. For each of the forward and reverse reads, one copy of the tandem duplication does not align to the reference. The unaligned copy and the subsequent portion of the read are soft-clipped. In the example of FIG. 3, for the forward read and reverse read, one copy of the tandem duplication portion is mapped, indicated by the "match" portion, and the other copy and subsequent portion of the read are soft-clipped, indicated by the "softclip" portion. The BAM file may include the sequences of the partially mapped reads and mark the soft-clipped portions.

Figure 4:
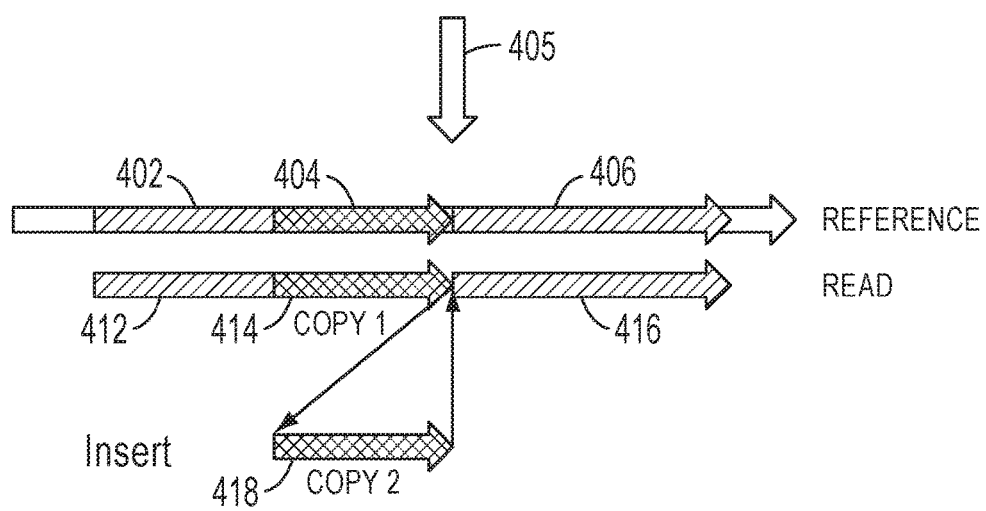
FIG. 4 illustrates an example of an arrangement of a read-to-reference alignment where both flanks of the tandem duplications are aligned with the reference.

FIG. 4 illustrates an example of an arrangement of a read-to-reference alignment where both flanks of the tandem duplications are aligned with the reference. In this example, the mapping or alignment process aligns the flank portion 412, "copy 1" portion 414 and flank portion 416 of the tandem duplication in the read with corresponding portions 402, 404 and 406 of the reference. This situation may occur for short inserts (e.g. less than 10 basepairs). The "copy 2" insert portion 418 of the read does not map to the reference, but may be detected by a variant caller in the standard pipeline. In some embodiments, a maximum insert length when both flanks are mapped to the reference depends on mapping or alignment process. Normally gaps of over 20-30 bp are not aligned reliably. For example, a default configuration for Torrent Mapping Alignment Program (TMAP) may support an insert of up to 50 bp under certain conditions. An insert of up to 50 bp can be reached when the read is long and both sides of the insert contain flank sequences having 35 bases or more that match the reference.

Figure 5:
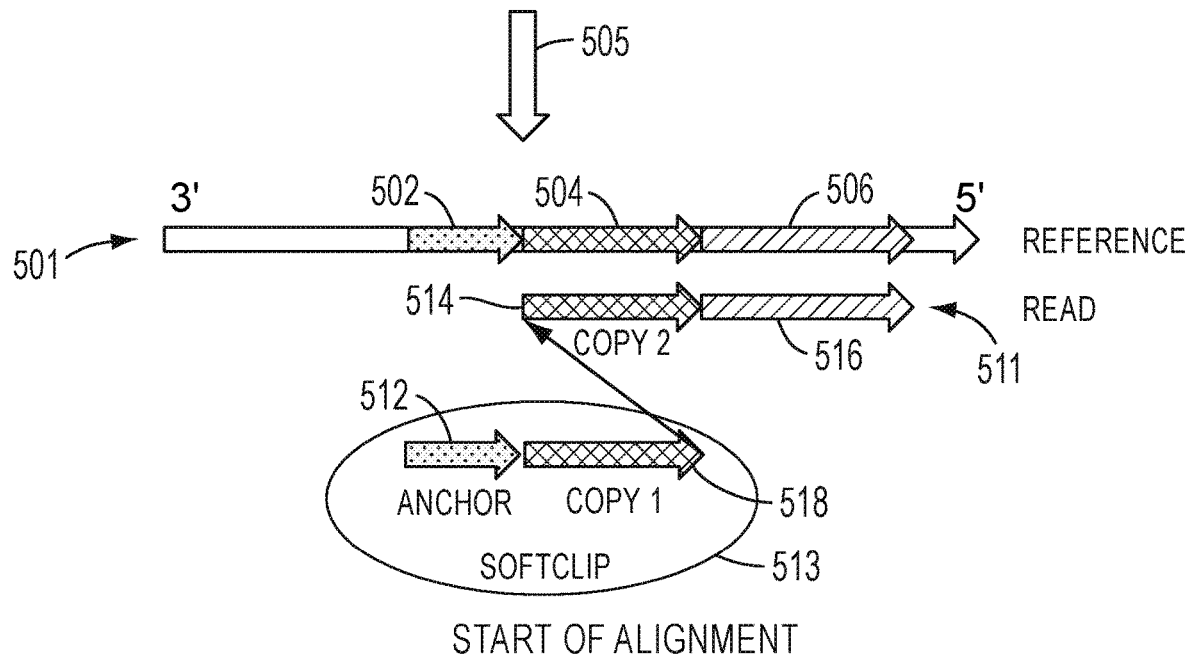
FIG. 5 illustrates an example of a "Start of alignment" arrangement of read-to-reference alignments for reads with a duplication insert.
Figure 6:
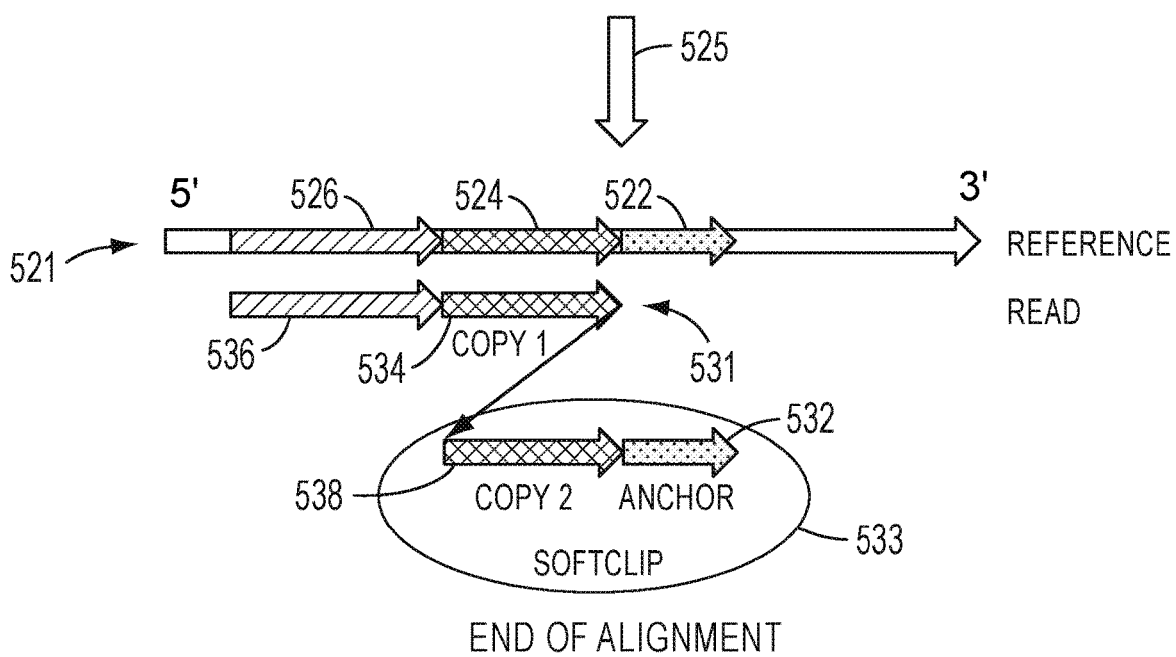
FIG. 6 illustrates an example of an "End of alignment" arrangement of read-to-reference alignments for reads with a duplication insert.

FIG. 5 illustrates an example of a "Start of alignment" arrangement of read-to-reference alignments for reads with a duplication insert. The "Start of alignment" example corresponds to a case where the read maps to a reverse strand of a reference 501. For this case, the soft-clipped portion 513 occurs before the aligned, or mapped, portion 511. FIG. 6 illustrates an example of an "End of alignment" arrangement of read-to-reference alignments for reads with a duplication insert. The "End of alignment" example corresponds to a case where the read maps to a forward strand of a reference 521. For this case, the soft-clipped portion 533 occurs after the aligned, or mapped, portion 531. The alignments in FIG. 5 and FIG. 6 are shown in the direction they are recorded in a BAM file, with the "Start of alignment" in reverse direction (3'→5'), and the "End of alignment" in forward direction (5'→3'). The upper lines of arrows depict the references 501 and 521, and the lower two lines of arrows depict the mapped portions 511 and 531 and the unmapped, or soft-clipped, portions 513 and 533 of the partially mapped reads. The soft-clipped portions 513 and 533, of the reads are shown below the mapped portions 511 and 531, respectively, (as if it is dropped from the alignments). The duplicated fragment in the "Start of alignment" example corresponds to the portion 504 in the reference 501, "copy 2" portion 514 in the mapped portion 511 and "copy 1" portion 518 in the soft-clipped portion 513. In the "End of alignment" example of FIG. 6, the duplicated fragment corresponds to the portion 524 in the reference 521, "copy 1" portion 534 in the mapped portion 531 and "copy 2" portion 538 in the soft-clipped portion 533. The duplicated fragment appears once in the reference, but twice in the read. The part of the mapped portion 511 of the read upstream (5') of the duplication is shown by portion 516, and its match on the reference 501 is shown by portion 506, in the "Start of alignment" example of FIG. 5. In the "End of alignment" example of FIG. 6, the part of the mapped portion 531 of the read upstream (5') of the duplication is shown by portion 536, and its match on the reference 521 is shown by portion 526. The portion of the read past the insert 518 and 538 on the soft-clipped portion 513 and 533, respectively, is referred to as an anchor portion 512 and 532, respectively. The anchor portion 512 matches portion 502 on the reference 501 in the "Start of alignment" example. The anchor portion 532 matches portion 522 on the reference 521 in the "End of alignment" example. The remaining portions of the reference 501 surrounding the portions that match the read are shown to the left of portion 502 and to the right of portion 506 for the "Start of alignment" example. The remaining portions of the reference 521 surrounding the portions that match the read are shown to the left of portion 526 and to the right of portion 522 for the "End of alignment" example.

According to an embodiment, an internal tandem duplication (ITD) detection algorithm analyzes the reads with long soft-clips on 3' ends. The algorithm can check the reads for the presence of an anchor at the 3' that matches the reference zone next to the alignment edge. The offset of the anchor on the read may determine insert size. The algorithm can further check the reads for the presence of duplication in the read such as where a first copy appears in the mapped portion and the second copy appears in the soft-clipped zone. The distance between copies may determine the duplication size. Such a test can detect even partially captured duplications, in which read does not cover the insert completely. Also, in an embodiment, the algorithm considers the well-mapped inserts, that have both flanks aligned, such as in the example of FIG. 4. For every position in the reference, the algorithm counts the inserts of each size that occurs in any covering reads. After all reads are seen, these counts represent the detected allele frequencies of the observed inserts For example for a forward read, a long soft-clip on 3' end corresponds to the "end of alignment" in FIG. 6. The algorithm can check the read for the presence of an anchor 532, that matches the reference zone next to the alignment edge, such as the reference portion 522. The offset of the anchor 532 from the alignment edge on the read may determine insert size. The algorithm can further check the read for the presence of duplication in the read such as where a first copy, such as "copy 1" 534, appears in the mapped portion 531 and the second copy, such as "copy 2" 538, appears in the soft-clipped portion 533.

For example for a reverse read, a long soft-clip on 3' end corresponds to the "start of alignment" in FIG. 5. Similar to the above, the algorithm can check the read for the presence of an anchor 512 that matches the reference zone next to the alignment edge, such as the reference portion 502. The offset of the anchor 512 from the alignment edge on the read may determine insert size. The algorithm can further check the read for the presence of duplication in the read such as where a first copy, such as "copy 1" 518, appears in the soft-clipped portion 513 and the second copy, such as "copy 2" 514, appears in the mapped portion 511.

According to an embodiment, an ITD detection algorithm may be performed by a processor according to the pseudo-code algorithm outline given in Table 1. The order of the steps is exemplary and different orders of steps are possible within the scope of the invention, as described in the claims.

TABLE 1

| STEPS |
| --- |
| 1 For each column in pileup: |
| 2     For each read intersecting the column: |
| 3         If contains Insert: |
| 4             Optionally filter by size |
| 5             Optionally check for duplication |
| 6             Assign to category based on insert size |
| 7         If contains End of alignment / Softclip start: |
| 8             Check if softclip is of sufficient size |
| 9             Find anchor |
| 10            Check for duplication in read around this position |
| 11            Derive size from anchor; if not found, derive size from duplication |
| 12            Optionally filter by size/location/anchor/duplication properties |
| 13            Assign to a category based on size |
| 14         If contains Start of alignment / Softclip end |
| 15             Check if softclip is of sufficient size |
| 16             Find anchor |
| 17             Check for duplication in read around this position |

TABLE 1-continued

| STEPS | |
|---|---|
| 18 | Derive size from anchor; if not found, derive size from duplication |
| 19 | Optionally filter by size/location/anchor/duplication properties |
| 20 | Assign to a category based on size |
| 21 | Filter categories by number of members (absolute and relative |
| 22 | to coverage at this position) |
| 23 | Convert frequent categories into 'features' (normalize positions) |
| 24 | Record features for this position |
| 25 | Merge features that represent same insert Report |

In accordance with step 1, each column in a pileup is analyzed in accordance with steps 2 to 23. The aligned sequence read information for the pileup is available from a BAM file. The pileup indicates the reads aligned with the reference at the targeted locations for FLT3-ITD detection. According to step 2, each read intersecting a particular column in the pileup is analyzed in accordance with steps 3 to 20.

Step 3 may determine whether an insert is present at the position in the read corresponding to the column. For example, a variant caller in a standard processing pipeline may indicate an insert in a situation where both flanks are mapped and the insert sequence is recorded in the BAM file. FIG. 4 gives an example of an insert 418 ("copy 2"), at the position 405. If an insert is present, the insert may optionally be filtered based on its size in accordance with step 4. A minimum insert size may be set by the user, such as 8 bases, for example. For step 5, the insert may optionally be checked to determine whether it is a duplication of the mapped portion of the read adjacent to the insert. For example, referring to FIG. 4, the insert 418 ("copy 2") may be compared to the mapped portion 414 ("copy 1") of the read to determine whether it is a duplication. For step 6, the read having the insert may be assigned to a category based on insert size.

Step 7 may determine whether the position in the read corresponding to the column contains an end of alignment with the reference and a softclip start. Referring to the "end of alignment" example of FIG. 6, the position of the end of alignment and softclip start is indicated by the breakpoint 525. Step 8 may determine whether the softclip has a sufficient size. A sufficient softclip size may be set by the user, for example 8-10 bases. Step 9 finds the anchor in the soft-clipped portion of the read and the reference. For the example of FIG. 6, the soft-clipped portion 533 of the read and the portion of the reference 521 after the breakpoint 525 are compared to find the matching portions that indicate the anchor 532 in the read and the anchor portion 522 of the reference. A string-matching method may be applied to the soft-clipped portion and unmapped reference portion adjacent to the breakpoint to determine matching anchor portions. The string-matching method may provide the length of the anchor, the position of the anchor in the read and the position of the anchor in the reference. A minimum anchor length may be set by the user, for example 12 bases. TABLE 2 gives an example of finding the anchor positions in the read and reference and the anchor length implemented by code in a Python programming language.

TABLE 2

| | |
|---|---|
| 1 | # perform anchor detection |
| 2 | ref_start = ref_pos |
| 3 | ref_end = min (ref_pos + query_length − query_position + p.anchor_ext, reference_len) |
| 4 | ref_seq = reference.fetch (ref_name, ref_start, ref_end) |
| 5 | query_start = query_position |
| 6 | query_end = query_length |
| 7 | anchor_pos_ref, anchor_pos_read, anchor_len = find_match (ref_seq, 0, len (ref_seq), |
| 8 | query_sequence, query_start, query_end) |
| 9 | if anchor_len >= p.min_anchor_len: # anchor is long enough |

Step 10 checks for duplication in the read around the position intersecting to the column. For the example of FIG. 6, the soft-clipped portion 533 of the read and the mapped portion 531 of the read before the breakpoint 525 are compared to find the matching portions that indicate "copy 1" 534 and "copy 2" 538 of the tandem duplication in the read. A string-matching method may be applied to the soft-clipped portion 533 and the mapped portion 531 adjacent to the breakpoint 525 to determine the matching portions of the read. The string-matching method may provide the offsets relative to the breakpoint of the tandem duplications, e.g. "copy 1" 534 and "copy 2" 538, relative to the breakpoint 525. The string-matching method may also provide the length of the matching portion. TABLE 3 gives an example of finding the offsets of the tandem duplication around the breakpoint implemented by code in a Python programming language.

TABLE 3

| | |
|---|---|
| 1 | # perform duplication detection (in read around break point) |
| 2 | dist_to_tail, dist_from_tail, dup_len = max_dup (query_sequence, query_position) |

Step 11 may derive the size of the insert using the anchor position. The size of the insert can be determined by the distance from the breakpoint to the anchor position in the soft-clipped portion. TABLE 4 gives an example of determining the insert size based on the anchor position implemented by code in a Python programming language.

TABLE 4

| | |
|---|---|
| 1 | # find insert size from anchor |
| 2 | anchor_off_ref = anchor_pos_ref |
| 3 | anchor_off_read = anchor_pos_read − query_start |
| 4 | if anchor_off_read − anchor_off_ref >= p.min_indel_len: |
| 5 | ins_size_by_anchor = anchor_off_read − anchor_off_ref |
| 6 | ins_pos_read_by_anchor = query_start |

If the anchor length is less than the minimum anchor length, the size of the insert may not be determined based on the anchor position. For this situation, the offsets determined by the duplication detection may be used to calculate the size of the insert. The size of insert is the distance from the start of the first occurrence of the duplicated fragment to the start of the second one. TABLE 5 gives an example of determining the insert size based on the duplication detection implemented by code in a Python programming language.

TABLE 5

| | |
|---|---|
| 1 | # find insert size and position from duplication |
| 2 | ins_size_by_dup = dup_len + dist_to_tail + dist_from_tail |
| 3 | ins_pos_read_by_dup = query_position − ins_size_by_dup |

A partial duplication, where the soft-clipped copy is truncated, may also be evaluated. A minimum duplication size, e.g. 10 bases, may be set by the user.

Step 12 may optionally filter by size, location, anchor properties and/or duplication properties based on user preferences. For example, a partially mapped read may be filtered out based on various conditions, such as the following:
1) anchor length is below threshold;
2) duplicated copies are not more than a certain number of bases apart;
3) duplicated copy size is above a threshold;
4) duplication start is not closer than a certain number of bases to the read edge;
5) number of mismatches in the duplicated copies is greater than a maximum number of mismatches.

Step 13 may assign the read to a category based on the insert size determined for the read. Each read having evidence of a particular insert size at a given column is assigned to the same category. There may be multiple insert sizes possible for reads intersecting a given column.

Step 14 may determine whether the position in the read corresponding to the column contains a start of alignment with the reference and a softclip end. Referring to the "start of alignment" example of FIG. 5, the position of the start of alignment and softclip end is indicated by the breakpoint 505. The steps for the start of alignment situation are adapted for the arrangement of the soft-clipped portion relative to the mapped portion of the read, as illustrated in FIG. 5. In step 15, softclip may be checked for sufficient size. Step 16 may find the anchor in the soft-clipped portion of read and the reference. For the example of FIG. 5, the soft-clipped portion 513 of the read and the portion of the reference 501 before the breakpoint 505 are compared to find the matching portions that indicate the anchor 512 in the read and the anchor portion 502 of the reference. A string-matching method may be applied to the soft-clipped portion and unmapped reference portion adjacent to the breakpoint to determine matching anchor portions, as described above with respect to step 9. The string-matching method may provide the length of the anchor, the position of the anchor in the read and the position of the anchor in the reference. A minimum anchor length may be set by the user, for example 12 bases. TABLE 6 gives an example of finding the anchor positions in the read and reference and the anchor length implemented by code in a Python programming language.

TABLE 6

| | |
|---|---|
| 1 | # perform anchor detection |
| 2 | ref_start = max (0, ref_pos − query_position − p.anchor_ext) |
| 3 | ref_end = ref_pos |
| 4 | ref_seq = reference.fetch (ref_name, ref_start, ref_end) |
| 5 | query_start = 0 |
| 6 | query_end = query_position |
| 7 | anchor_pos_ref, anchor_pos_read, anchor_len = find_match |
| 8 | (ref_seq, 0, len (ref_seq), query_sequence, query_start, query_end) |
| 9 | if anchor_len >= p.min_anchor_len: # anchor is long enough |

Step 17 may check for duplication in the read around the position intersecting to the column. For the example of FIG. 5, the soft-clipped portion 513 of the read and the mapped portion 511 of the read after the breakpoint 505 are compared to find the matching portions that indicate "copy 1" 518 and "copy 2" 514 of the tandem duplication in the read. A string-matching method may be applied to the soft-clipped portion 513 and the mapped portion 511 adjacent to the breakpoint 505 to determine the matching portions of the read. The string-matching method may provide the offsets relative to the breakpoint of the tandem duplications, e.g. "copy 1" 518 and "copy 2" 514, relative to the breakpoint 505. The string-matching method may also provide the length of the matching portion. TABLE 7 gives an example of finding the offsets of the tandem duplication around the breakpoint implemented by code in a Python programming language.

TABLE 7

| | |
|---|---|
| 1 | # perform duplication detection (in read around break point) |
| 2 | dist_to_head, dist_from_head, dup_len = max_dup (query_sequence, query_position) |

Step 18 may derive the size of the insert using the anchor position. The size of the insert can be determined by the distance from the breakpoint to the anchor position in the soft-clipped portion. TABLE 8 gives an example of determining the insert size based on the anchor position implemented by code in a Python programming language.

TABLE 8

| | |
|---|---|
| 1 | # find insert size and position from anchor |
| 2 | anchor_off_ref = len (ref_seq) − anchor_pos_ref |
| 3 | anchor_off_read = query_end − anchor_pos_read |
| 4 | if anchor_off_read − anchor_off_ref >= p.min_indel_len: |
| 5 | ins_size_by_anchor = anchor_off_read − anchor_off_ref |
| 6 | ins_pos_read_by_anchor = anchor_pos_read + anchor_off_ref |

If the anchor length is less than the minimum anchor length, the size of the insert may not be determined based on the anchor position. For this situation, the offsets determined by the duplication detection may be used to calculate the size of the insert. The size of insert is the distance from the start of the first occurrence of the duplicated fragment to the start of the second one. TABLE 9 gives an example of determining the insert size based on the duplication detection implemented by code in a Python programming language.

TABLE 9

| | |
|---|---|
| 1 | # find insert size and position from duplication |
| 2 | ins_size_by_dup = dist_to_head + dup_len + dist_from_head |
| 3 | ins_pos_read_by_dup = query_position − ins_size_by_dup |

A partial duplication, where the soft-clipped copy is truncated, may also be evaluated. A minimum duplication size, e.g. 10 bases, may be set by the user.

Step 19 may optionally filter by size, location, anchor properties and/or duplication properties based on user preferences, as described above with respect to step 12. For example, certain duplications may be filtered out if the number of mismatches in the duplications is greater than a maximum number of mismatches.

Step 20 may assign the read to a category based on the insert size determined for the read. Each read having evidence of a particular insert size at a given column is assigned to the same category. There may be multiple insert sizes possible for reads intersecting a given column.

TABLE 10 gives an example of the function "find_match" used in the anchor detection code examples given in TABLE 2 and TABLE 6, and used in the example of merging features given in Table 12 below, implemented by code in a Python programming language.

TABLE 10

```
1   def find_match (seq1, beg1, end1, seq2, beg2, end2):
2     """
3     returns (coord1, coord2, len) of the longest exact match
4     where shift1 is offset from end of first duplicate to the division
5     point, shift2 is offset from the division point to second dup
6     """
7     match = difflib.SequenceMatcher
8     (None, seq1, seq2, False).find_longest_match (beg1, end1, beg2,
         end2)
9     return match
```

TABLE 11 gives an example of the function "max_dup" in the duplication detection code examples given in TABLE 3 and TABLE 7 implemented by code in a Python programming language.

TABLE 11

```
1   def max_dup (sequence, division_point):
2     """
3     returns triplet: shift1, shift2, length
4     where shift1 is offset from end of first duplicate to the division
5     point, shift2 is offset from the division point to the beginning of
         second dup
6     """
7     try:
8       match = difflib.SequenceMatcher
9     (None, sequence, sequence, False).find_longest_match (0,
         division_point, division_point, len (sequence))
10    return division_point – (match.a + match.size), match.b –
         division_point, match.size
```

In line 8 of TABLE 11, "difflib" is a Python library function for string-matching. Various aspects of string-matching methods are described in Boyer, Robert S. and Moore, J. Strother, (October 1977) "A fast string searching algorithm," Communications of the ACM. 20:10. pp. 762-772 (DOI:10.1145/359842.359859).

Step 21 may filter the categories for each column based on the number of members in the category using an absolute count and a count relative to coverage at this position. For example, a minimum count may be set to 4. A coverage fraction is a ratio of the number of members in the category to coverage at the insert position. For example, a minimum coverage fraction may be set to 0.0025. The minimum count and minimum coverage fraction can be set by the user. Categories having a number of members that do not meet the minimum count or the minimum coverage fraction may be filtered away.

Step 22 may convert the frequent categories into 'features' and normalize positions of the features. A feature comprises descriptive information such as an insert of certain size and content that occurs at a certain position.

Step 23 may record the features present for this position. For each position corresponding to a column in the pileup, the features present at the position are recorded.

Step 24 may merge features that represent the same insert. The features may be merged using single link clustering, a type of disjoint set computing algorithm. The features are considered linked if they occur at compatible locations, i.e. at least one edge of the first feature appears in given proximity to any of the edges of the second feature, have a similar size below a given threshold and have matching content on over a certain fraction of their size. TABLE 12 gives an example of merging features using single-link clustering implemented by code in a Python programming language.

TABLE 12

```
1   # cluster positions – within a segment
2   # put all registered inserts in one array; remember coverages of all registered positions
3   inserts = [ ]
4   for position, coverage, tags in features:
5     for tag, size, cnt, wt, seq in tags:
6       inserts.append ((position, size, cnt, wt, seq, coverage))
7   # Do single-link clustering. The link requirements:
8   # – pos1 ~ pos2 && size1 ~ size2 and content matches
9   # or
10  # – size1 ~ size2 && abs (pos1 – pos2) ~ size and content matches
11  djs = DJS (len (inserts))
12  for i1, (pos1, sz1, cnt1, wt1, seq1, cov1) in enumerate (inserts):
13    for i2, (pos2, sz2, cnt2, wt2, seq2, cov2) in enumerate (inserts):
14      if i2 == i1:
15        break
16      if abs (pos1 – pos2) <= p.pos_tol:
17        if abs (sz1 – sz2) <= p.pos_tol:
18          # check content – require exact match on intersection
19          c1, c2, match_len = find_match (seq1, 0, sz1, seq2, 0, sz2)
20          if match_len + p.pos_tol >= min (sz1, sz2):
21            djs.bind (i1, i2)
22          else:
23            minors = True
24      elif abs (abs (pos1 – pos2) – sz1) <= p.pos_tol or abs (abs (pos1 – pos2) – sz2) <=
25  p.pos_tol: # tandem repeat
26        if abs (sz1 – sz2) <= p.pos_tol:
27          # check content – require exact match on intersection
28          c1, c2, match_len = find_match (seq1, 0, sz1, seq2, 0, sz2)
29          if match_len + p.pos_tol >= min (sz1, sz2):
30            djs.bind (i1, i2)
31    groups = djs.resolve ( )
32    # now store these with the segment
33    segment_results.append ((inserts, groups))
```

Various aspects of single-link clustering and disjoint set computing algorithms are described in Galler, Bernard A.; Fischer, Michael J. (May 1964) "An improved equivalence algorithm," Communications of the ACM. 7. pp. 301-303 (DOI:10.1145/364099.364331); Hoperoft, J. E.; Ullman, J. D. (1973), "Set Merging Algorithms," SIAM Journal on Computing, 2 (4): 294-303 (DOI:10.1137/0202024); Tarjan, Robert E.; van Leeuwen, January (1984). "Worst-case analysis of set union algorithms," Journal of the ACM. 31 (2): 245-281 (DOI:10.1145/62.2160); and Galil, Z., Italiano, G. (1991), "Data structures and algorithms for disjoint set union problems," ACM Computing Surveys, 23: 319-344 (DOI:10.1145/116873.116878).

Step 25 may generate a report of FLT3-ITD detection results for the user.

Figure 7:
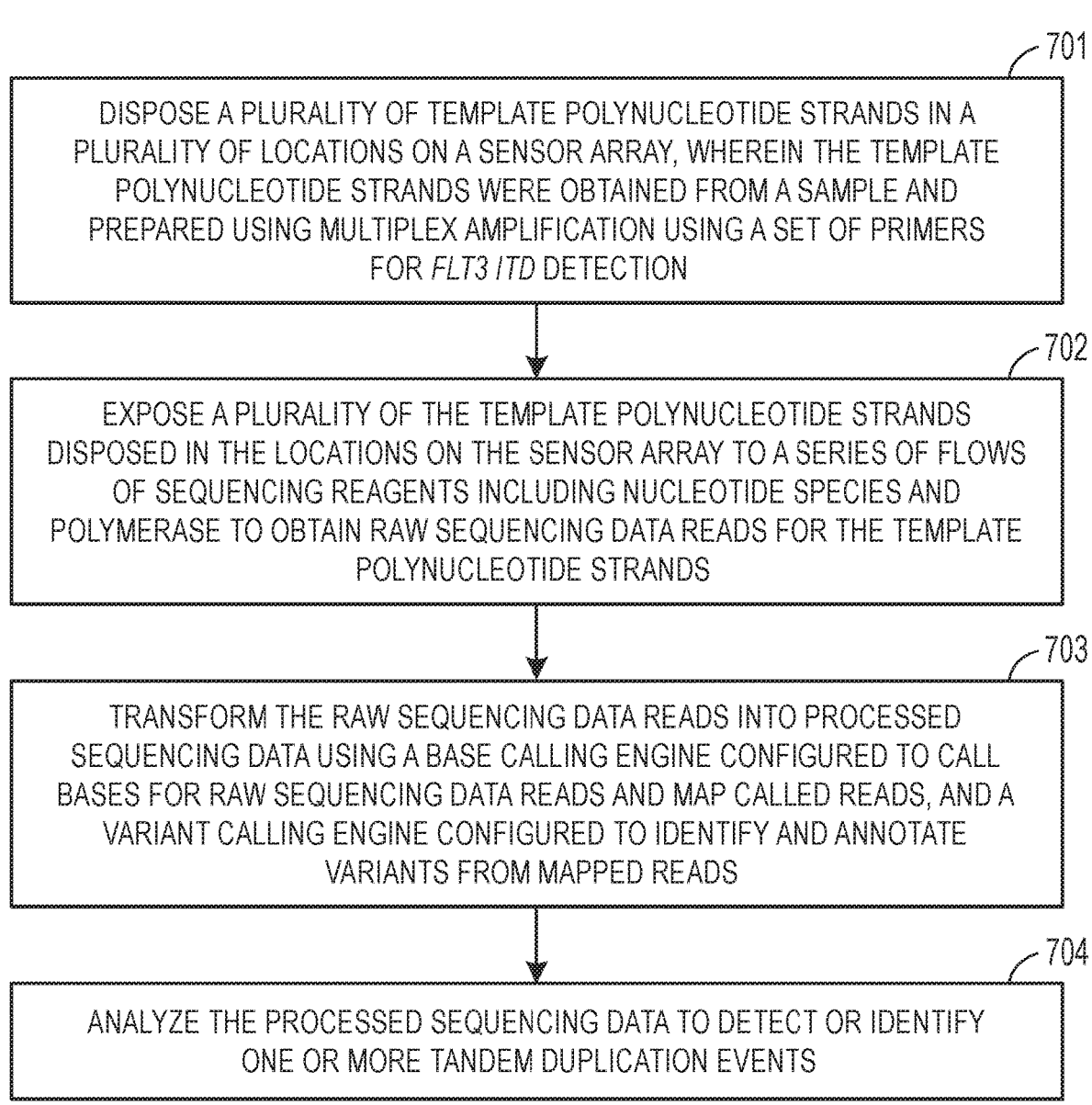
FIG. 7 illustrates an exemplary method for detecting tandem duplication.

FIG. 7 illustrates an exemplary method for detecting tandem duplication. In step 701, a plurality of template polynucleotide strands are disposed in a plurality of locations on a sensor array, and the template polynucleotide strands were obtained from the sample and prepared using multiplex amplification using a set of primers for FLT3 detection. In step 702, a plurality of the template polynucleotide strands disposed in the locations on the sensor array are exposed to a series of flows of sequencing reagents including nucleotide species and polymerase to obtain raw sequencing data reads for the template polynucleotide strands. In step 703, the raw sequencing data reads are transformed into processed sequencing data using a base calling engine configured to call bases for raw sequencing data reads and map called reads, and a variant calling engine configured to identify and annotate variants from mapped reads. In step 704, the processed sequencing data are analyzed to detect or identify one or more tandem duplication events using methods described herein.

Results of the duplication detection methods described herein are compared with those of the variant caller of a standard pipeline. Testing was applied to samples of engineered constructs of DNA fragments, including known locations and lengths of inserts to simulate FLT3-ITD structures. The DNA fragments were amplified and processed by a nucleic acid sequencing system, including base calling, mapping and variant calling. TABLE 13 shows results of testing the samples.

TABLE 13

| SAMP NO. | KNOWN INSERT LOCATION | | | VARIANT CALLER | ITD DETECTION | |
|---|---|---|---|---|---|---|
| | FWD | REV | SIZE | SIZE | SIZE | % READS |
| 1 | 04 | 8262 | 8311 | 49 | 49 (Ins) | 48 | 11.6% |
| 2 | | | | | 48 (Dup) | 48 | 13.8% |
| 3 | 08 | 8263 | 8288 | 25 | 25 | 25 | 8.3% |
| 4 | | | | | | 25 | 7.1% |
| 5 | 03 | 8262 | 8327 | 64 | NO DET | 63 | 16.4% |
| 6 | | | | | | 63 | 17.5% |
| 7 | | | | | | 64 | 6.7% |
| 8 | | | | | | 65 | 2.2% |
| 9 | 11 | 8262 | 8280 | 18 | 18 | 18 | 9.6% |
| 10 | | | | | | 18 | 12.2% |
| 11 | 06 | 8262 | | 24 | 24 | 24 | 9.8% |
| 12 | | | | | | 24 | 14.7% |
| 13 | | | | | | 23 | 1.5% |
| 14 | | | | | | 23 | 1.3% |
| 15 | 21 | 8226 | 8289 | 64 | NO DET | 64 | 21.3% |
| 16 | | | | | | 64 | 15.3% |
| 17 | 01 | 2625 | 2629 | 33 | 27 | 27 | 12.3% |
| 18 | | | | | | 27 | 16.0% |
| 19 | 26 | 8086 | 8130 | 114 | NO DET | 113-120 | 27% |
| 20 | | | | | | 113-120 | 27% |
| 21 | 27 | 8099 | 8130 | 64 | 64 | 63 | 2.4% |
| 22 | | | | | | 63 | 10.4% |
| 23 | | | | | | 64 | 1.7% |
| 24 | | | | | | 64 | 11.1% |
| 25 | 28 | 8127 | | 70 | 70 | 69-71 | 25.7% |
| 26 | | | | | | 69-71 | 18.4% |
| 27 | 18 | 8226 | 8290 | 193 | 1 | 97 (half) | 0.4% |
| 28 | | | | | | 97 (half) | 0.3% |
| 29 | 19 | 8226 | 8290 | 97 | 1 | 98 | 0.9% |
| 30 | | | | | | 98 | 1.2% |
| 31 | 14 | 8230 | 8261 | 33 | 31 | 31 | 8/1% |
| 32 | | | | | | 31 | 7.7% |
| 33 | 15 | 8232 | 8248 | 18 | 16 | 18 | 9.6% |
| 34 | | | | | | 18 | 12.2% |
| 35 | 15 | 8232 | 8248 | 16 | 16 | 16 | 7.3% |
| 36 | | | | | | 16 | 6.9% |
| 37 | 16 | 8368 | | 18 | 19 | 18 | 5.6% |
| 38 | | | | | | 18 | 3.6% |
| 39 | | | | | | 19 | 1.2% |

The KNOWN INSERT columns give the location of the insert in the forward read, the location of the insert in the reverse read and the insert size. The VARIANT CALLER column gives the results of the insert sizes determined by a variant caller of the standard pipeline. The ITD DETECTION columns give the results of the insert size determined by duplication detection described herein. The % READS column gives the percentage of the total reads where the tandem duplication was detected. The results of multiple tests on the same sample are shown. The above results show that the duplication detection method was successful for samples where the variant caller failed to detect (NO DET) the insert, e.g. for samples 03 (insert size=64), 21 (insert size=64) and 26 (insert size=114). For sample 18 (insert size=193), the variant caller result was insert size=1, while the duplication detection method result was insert size=97, half the true size of the insert. For sample 19 (insert size=97), the variant caller result was insert size=1, while the duplication detection method result was insert size=98. These results show that, particularly for samples with longer insert sizes, the duplication detection method provides improvement in accuracy over the variant caller of a standard pipeline.

According to an exemplary embodiment, there is provided a method for detecting an internal tandem duplication in an FLT3 gene of a sample, comprising: (a) amplifying a nucleic acid sample in the presence of a primer pool to produce a plurality of amplicons, the primer pool including a plurality of target specific primers targeting regions of exons of the FLT3 gene; (b) sequencing the amplicons to generate a plurality of reads; (c) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (d) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (e) converting the categories into features corresponding to the column, wherein a feature includes the insert size and a sequence of an insert at an insert position; and (f) merging the features corresponding to one or more columns representing a same insert to determine a location and a size of a tandem duplication. The step of analyzing the partially mapped reads intersecting a column of the pileup further comprises determining whether the partially mapped read intersects the column at the breakpoint representing an end of alignment and a start of the soft-clipped portion, wherein the partially mapped read is a forward read. The step of analyzing the partially mapped reads intersecting a column of the pileup further comprises determining whether the partially mapped read intersects the column at the breakpoint representing a start of alignment and an end of the soft-clipped portion, wherein the partially mapped read is a reverse read. The step of analyzing the partially mapped reads intersecting a column of the pileup further comprises determining an anchor portion of the soft-clipped portion that matches a portion of the reference sequence adjacent to the breakpoint. The step of determining an anchor portion further comprises applying a string-matching method to the soft-clipped portion and an unmapped portion of the reference sequence adjacent to the breakpoint. The step of determining an insert size of the duplication is based on a distance from the breakpoint to a position of the anchor portion in the soft-clipped portion. The step of detecting a duplication applies a string-matching method to the soft-clipped portion and the mapped portion adjacent to the breakpoint. The method further comprises filtering the categories for each column based on the number of members in the category. The step of filtering is based on an absolute count of the number of members in the category. The step of filtering is based on a ratio of the number of members in the category to a coverage at the insert position. The step of merging the features further comprises applying a single-link clustering to the features.

According to an exemplary embodiment, there is provided a system for detecting an internal tandem duplication in an FLT3 gene of a sample, comprising a machine-readable memory and a processor configured to execute machine-readable instructions, which, when executed by the processor, cause the system to perform a method, comprising: (a) receiving a plurality of reads, wherein the plurality of reads correspond to a plurality of targeted regions of exons of the FLT3 gene; (b) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (c) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (d) converting the categories into features corresponding to the column, wherein a feature includes the insert size and a sequence of an insert at an insert position; and (e) merging the features corresponding to one or more columns representing a same insert to determine a location and a size of a tandem duplication. The step of analyzing the partially mapped reads intersecting a column of the pileup further comprises determining whether the partially mapped read intersects the column at the breakpoint representing an end of alignment and a start of the soft-clipped portion, wherein the partially mapped read is a forward read. The step of analyzing the partially mapped reads intersecting a column of the pileup further comprises determining whether the partially mapped read intersects the column at the breakpoint representing a start of alignment and an end of the soft-clipped portion, wherein the partially mapped read is a reverse read. The step of analyzing the partially mapped reads intersecting a column of the pileup further comprises determining an anchor portion of the soft-clipped portion that matches a portion of the reference sequence adjacent to the breakpoint. The step of determining an anchor portion further comprises applying a string-matching method to the soft-clipped portion and an unmapped portion of the reference sequence adjacent to the breakpoint. The step of determining an insert size of the duplication is based on a distance from the breakpoint to a position of the anchor portion in the soft-clipped portion. The step of detecting a duplication applies a string-matching method to the soft-clipped portion and the mapped portion adjacent to the breakpoint. The method further comprises filtering the categories for each column based on the number of members in the category. The step of filtering is based on an absolute count of the number of members in the category. The step of filtering is based on a ratio of the number of members in the category to a coverage at the insert position. The step of merging the features further comprises applying a single-link clustering to the features.

According to an exemplary embodiment, there is provided a computer-readable media comprising machine-readable instructions that, when loaded in a machine-readable memory and executed by a processor, are configured to cause a system to perform a method for detecting an internal tandem duplication in an FLT3 gene of a sample, comprising: (a) receiving a plurality of reads, wherein the plurality of reads correspond to a plurality of targeted regions of exons of the FLT3 gene; (b) mapping the reads to a reference sequence, wherein the reference sequence includes the targeted regions of exons of the FLT3 gene, wherein the mapping produces a pileup comprising a plurality of alignments of the reads with the reference sequence and a plurality of columns corresponding to positions along the reference sequence, wherein a portion of the plurality of reads are partially mapped to the reference sequence for a plurality of partially mapped reads, wherein a partially mapped read includes a mapped portion, a soft-clipped portion and a breakpoint; (c) analyzing the partially mapped reads intersecting a column of the pileup for tandem duplications, including: (i) detecting a duplication in the soft-clipped portion by comparing the soft-clipped portion to the mapped portion adjacent to the breakpoint; (ii) determining an insert size of the duplication in the soft-clipped portion; (iii) assigning the partially mapped read to a category based on the insert size to generate a plurality of categories corresponding to a plurality of insert sizes, each category having a number of members corresponding to the partially mapped reads having the corresponding insert size; (d) converting the categories into features corresponding to the column, wherein a feature includes the insert size and a sequence of an insert at an insert position; and (e) merging the features corresponding to one or more columns representing a same insert to determine a location and a size of a tandem duplication. The step of analyzing the partially mapped reads intersecting a column of the pileup further comprises determining whether the partially mapped read intersects the column at the breakpoint representing an end of alignment and a start of the soft-clipped portion, wherein the partially mapped read is a forward read. The step of analyzing the partially mapped reads intersecting a column of the pileup further comprises determining whether the partially mapped read intersects the column at the breakpoint representing a start of alignment and an end of the soft-clipped portion, wherein the partially mapped read is a reverse read. The step of analyzing the partially mapped reads intersecting a column of the pileup further comprises determining an anchor portion of the soft-clipped portion that matches a portion of the reference sequence adjacent to the breakpoint. The step of determining an anchor portion further comprises applying a string-matching method to the soft-clipped portion and an unmapped portion of the reference sequence adjacent to the breakpoint. The step of determining an insert size of the duplication is based on a distance from the breakpoint to a position of the anchor portion in the soft-clipped portion. The step of detecting a duplication applies a string-matching method to the soft-clipped portion and the mapped portion adjacent to the breakpoint. The method further comprises filtering the categories for each column based on the number of members in the category. The step of filtering is based on an absolute count of the number of members in the category. The step of filtering is based on a ratio of the number of members in the category to a coverage at the insert position. The step of merging the features further comprises applying a single-link clustering to the features.

According to an exemplary embodiment, there is provided a method for detecting tandem duplication in a sample, comprising: (a) disposing a plurality of template polynucleotide strands in a plurality of locations on a sensor array, wherein the template polynucleotide strands were obtained from the sample and prepared using multiplex amplification using a set of primers for FLT3 detection; (b) exposing a plurality of the template polynucleotide strands disposed in the locations on the sensor array to a series of flows of sequencing reagents including nucleotide species and polymerase to obtain raw sequencing data reads for the template polynucleotide strands; (c) transforming the raw sequencing data reads into processed sequencing data using a base calling engine configured to call bases for raw sequencing data reads and map called reads, and a variant calling engine configured to identify and annotate variants from mapped reads; and (d) analyzing the processed sequencing data to detect or identify one or more tandem duplication events using methods described herein.

According to an exemplary embodiment, there is provided a system for detecting tandem duplication, including: a plurality of template polynucleotide strands in a plurality of locations on a sensor array, wherein the template polynucleotide strands were obtained from the sample and prepared using multiplex amplification using a set of primers for FLT3 detection; a machine-readable memory; and a processor configured to execute machine-readable instructions, which, when executed by the processor, cause the system to perform a method for detecting tandem duplication in a sample, comprising: (a) exposing a plurality of the template polynucleotide strands disposed in the locations on the sensor array to a series of flows of sequencing reagents including nucleotide species and polymerase to obtain raw sequencing data reads for the template polynucleotide strands; (b) transforming the raw sequencing data reads into processed sequencing data using a base calling engine configured to call bases for raw sequencing data reads and map called reads, and a variant calling engine configured to identify and annotate variants from mapped reads; and (c) analyzing the processed sequencing data to detect or identify one or more tandem duplication events using methods described herein.

According to an exemplary embodiment, there is provided a computer-readable media comprising machine-readable instructions that, when loaded in a machine-readable memory and executed by a processor, are configured to cause a system to perform a method for detecting tandem duplication in a sample, said method comprising: (a) exposing a plurality of the template polynucleotide strands disposed in a plurality of locations on the sensor array to a series of flows of sequencing reagents including nucleotide species and polymerase to obtain raw sequencing data reads for the template polynucleotide strands, wherein the template polynucleotide strands were obtained from the sample and prepared using multiplex amplification using a set of primers for FLT3 detection; (b) transforming the raw sequencing data reads into processed sequencing data using a base calling engine configured to call bases for raw sequencing data reads and map called reads, and a variant calling engine configured to identify and annotate variants from mapped reads; and (c) analyzing the processed sequencing data to detect or identify one or more tandem duplication events using methods described herein.

According to various embodiments, one or more features of teachings and/or embodiments described herein may be performed or implemented using appropriately configured and/or programmed hardware and/or software elements.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of teachings and/or embodiments described herein may be performed or implemented using an appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed, clustered, remote, or cloud architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

Unless otherwise specifically designated herein, terms, techniques, and symbols of biochemistry, cell biology, genetics, molecular biology, nucleic acid chemistry, nucleic acid sequencing, and organic chemistry used herein follow those of standard treatises and texts in the relevant field.

What is claimed is:

1. A method for detecting an internal tandem duplication in an FLT3 gene of a sample, comprising:
    amplifying a nucleic acid sample in a presence of a primer pool to produce a plurality of template polynucleotide strands, the primer pool including a plurality of target specific primers targeting regions of exons of the FLT3 gene;
    disposing the plurality of template polynucleotide strands in a plurality of reaction confinement regions on a sensor array, wherein the sensor array comprises at least $10^5$ sensors in electrical communication with the reaction confinement regions;
    exposing a plurality of the template polynucleotide strands disposed in the reaction confinement regions on the sensor array to a series of flows of sequencing reagents including nucleotide species and polymerase to obtain raw sequencing data reads for the template polynucleotide strands;
    determining base sequences of the raw sequencing data reads by base calling to generate a plurality of reads, wherein the plurality of reads includes a plurality of forward reads and a plurality of reverse reads;
    mapping the forward reads and the reverse reads to a reference genome, wherein the reference genome includes the targeted regions of exons of the FLT3 gene, wherein the mapping produces a pileup comprising a plurality of alignments of the forward reads and the reverse reads with the reference genome and a plurality of columns corresponding to positions along the reference genome, wherein a portion of the plurality of forward reads and the plurality of reverse reads are partially mapped to the reference genome for a plurality of partially mapped reads, wherein a partially mapped read includes a mapped portion, a soft-clipped portion and a breakpoint;
    analyzing the partially mapped reads intersecting a column of the pileup for tandem duplications, including:
        detecting a duplication in the soft-clipped portion by comparing a sequence of the soft-clipped portion to a sequence of the mapped portion of the partially mapped read adjacent to the breakpoint;
        determining an insert size of the duplication in the soft-clipped portion;
        filtering the detected duplications based on properties of duplicated copies to form filtered partially mapped reads;
        assigning the filtered partially mapped read to a category based on the insert size to generate a plurality of categories corresponding to a plurality of insert sizes, each category having a number of members corresponding to the filtered partially mapped reads having the corresponding insert size;
        converting the categories into features corresponding to the column, wherein a feature includes the insert size and a sequence of an insert at an insert position; and
        merging the features corresponding to one or more columns representing a same insert to determine a location and a size of a tandem duplication.

2. The method of claim 1, wherein the analyzing the partially mapped reads intersecting a column of the pileup further comprises determining whether the partially mapped read intersects the column at the breakpoint representing an end of alignment and a start of the soft-clipped portion, wherein the partially mapped read is a forward read.

3. The method of claim 1, wherein the analyzing the partially mapped reads intersecting a column of the pileup further comprises determining whether the partially mapped read intersects the column at the breakpoint representing a start of alignment and an end of the soft-clipped portion, wherein the partially mapped read is a reverse read.

4. The method of claim 1, wherein the analyzing the partially mapped reads intersecting a column of the pileup further comprises determining an anchor portion of the soft-clipped portion that matches a portion of the reference genome adjacent to the breakpoint.

5. The method of claim 4, wherein the determining an anchor portion further comprises applying a string-matching method to the soft-clipped portion and an unmapped portion of the reference genome adjacent to the breakpoint.

6. The method of claim 4, wherein the determining an insert size of the duplication is based on a distance from the breakpoint to a position of the anchor portion in the soft-clipped portion.

7. The method of claim 1, wherein the detecting a duplication applies a string-matching method to the soft-clipped portion and the mapped portion adjacent to the breakpoint.

8. The method of claim 1, further comprising filtering the categories for each column based on the number of members in the category.

9. The method of claim 8, wherein the filtering the categories is based on an absolute count of the number of members in the category.

10. The method of claim 8, wherein the filtering the categories is based on a ratio of the number of members in the category to a coverage at the insert position.

11. The method of claim 1, wherein the merging the features further comprises applying a single-link clustering to the features.

12. A system for detecting an internal tandem duplication in an FLT3 gene of a sample, comprising:
a plurality of template polynucleotide strands disposed in a plurality of reaction confinement regions on a sensor array, wherein the sensor array comprises at least $10^5$ sensors in electrical communication with the reaction confinement regions, wherein the template polynucleotide strands were obtained from the sample and prepared using multiplex amplification using a set of primers for FLT3 detection;
a machine-readable memory; and
a processor configured to execute machine-readable instructions, which, when executed by the processor, cause the system to perform a method, comprising:
exposing a plurality of the template polynucleotide strands disposed in the reaction confinement regions on the sensor array to a series of flows of sequencing reagents including nucleotide species and polymerase to obtain raw sequencing data reads for the template polynucleotide strands;
determining base sequences of the raw sequencing data reads by base calling to generate a plurality of reads wherein the plurality of reads includes a plurality of forward reads and a plurality of reverse reads;
mapping the forward reads and the reverse reads to a reference genome, wherein the reference genome includes targeted regions of exons of the FLT3 gene, wherein the mapping produces a pileup comprising a plurality of alignments of the forward reads and the reverse reads with the reference genome and a plurality of columns corresponding to positions along the reference genome, wherein a portion of the plurality of forward reads and the plurality of reverse reads are partially mapped to the reference genome for a plurality of partially mapped reads, wherein a partially mapped read includes a mapped portion, a soft-clipped portion and a breakpoint;
analyzing the partially mapped reads intersecting a column of the pileup for tandem duplications, including:
detecting a duplication in the soft-clipped portion by comparing a sequence of the soft-clipped portion to a sequence of the mapped portion of the partially mapped read adjacent to the breakpoint;
determining an insert size of the duplication in the soft-clipped portion;
filtering the detected duplications based on properties of duplicated copies to form filtered partially mapped reads;
assigning the filtered partially mapped read to a category based on the insert size to generate a plurality of categories corresponding to a plurality of insert sizes, each category having a number of members corresponding to the filtered partially mapped reads having the corresponding insert size;
converting the categories into features corresponding to the column, wherein a feature includes the insert size and a sequence of an insert at an insert position; and
merging the features corresponding to one or more columns representing a same insert to determine a location and a size of a tandem duplication.

13. The system of claim 12, wherein the analyzing the partially mapped reads intersecting a column of the pileup further comprises determining whether the partially mapped read intersects the column at the breakpoint representing an end of alignment and a start of the soft-clipped portion, wherein the partially mapped read is a forward read.

14. The system of claim 12, wherein the analyzing the partially mapped reads intersecting a column of the pileup further comprises determining whether the partially mapped read intersects the column at the breakpoint representing a start of alignment and an end of the soft-clipped portion, wherein the partially mapped read is a reverse read.

15. The system of claim 12, wherein the analyzing the partially mapped reads intersecting a column of the pileup further comprises determining an anchor portion of the soft-clipped portion that matches a portion of the reference genome adjacent to the breakpoint.

16. The system of claim 15, wherein the determining an insert size of the duplication is based on a distance from the breakpoint to a position of the anchor portion in the soft-clipped portion.

17. The system of claim 12, wherein the detecting a duplication applies a string-matching method to the soft-clipped portion and the mapped portion adjacent to the breakpoint.

18. The system of claim 12, further comprising filtering the categories for each column based on the number of members in the category.

19. The system of claim 12, wherein the merging the features further comprises applying a single-link clustering to the features.

20. A computer-readable media comprising machine-readable instructions that, when loaded in a machine-readable memory and executed by a processor, are configured to cause a system to perform a method for detecting an internal tandem duplication in an FLT3 gene of a sample, comprising:

exposing a plurality of template polynucleotide strands disposed on a sensor array to a series of flows of sequencing reagents including nucleotide species and polymerase to obtain raw sequencing data reads for the template polynucleotide strands, wherein the sensor array comprises at least $10^5$ sensors in electrical communication with reaction confinement regions, wherein the template polynucleotide strands were obtained from the sample and prepared using multiplex amplification using a set of primers for FLT3 detection;

determining base sequences of the raw sequencing data reads by base calling to generate a plurality of reads wherein the plurality of reads includes a plurality of forward reads and a plurality of reverse reads;

mapping the forward reads and the reverse reads to a reference genome, wherein the reference genome includes targeted regions of exons of the FLT3 gene, wherein the mapping produces a pileup comprising a plurality of alignments of the forward reads and the reverse reads with the reference genome and a plurality of columns corresponding to positions along the reference genome, wherein a portion of the plurality of forward reads and the plurality of reverse reads are partially mapped to the reference genome for a plurality of partially mapped reads, wherein a partially mapped read includes a mapped portion, a soft-clipped portion and a breakpoint;

analyzing the partially mapped reads intersecting a column of the pileup for tandem duplications, including:

detecting a duplication in the soft-clipped portion by comparing a sequence of the soft-clipped portion to a sequence of the mapped portion of the partially mapped read adjacent to the breakpoint;

determining an insert size of the duplication in the soft-clipped portion;

filtering the detected duplications based on properties of duplicated copies to form filtered partially mapped reads;

assigning the filtered partially mapped read to a category based on the insert size to generate a plurality of categories corresponding to a plurality of insert sizes, each category having a number of members corresponding to the filtered partially mapped reads having the corresponding insert size;

converting the categories into features corresponding to the column, wherein a feature includes the insert size and a sequence of an insert at an insert position; and merging the features corresponding to one or more columns representing a same insert to determine a location and a size of a tandem duplication.

\* \* \* \* \*

UNITED STATES PATENT AND TRADEMARK OFFICE
CERTIFICATE OF CORRECTION

| | | |
|---|---|---|
| PATENT NO. | : 11,961,591 B2 | Page 1 of 1 |
| APPLICATION NO. | : 16/206003 | |
| DATED | : April 16, 2024 | |
| INVENTOR(S) | : Denis Kaznadzey | |

It is certified that error appears in the above-identified patent and that said Letters Patent is hereby corrected as shown below:

In the Claims

In Column 25, Claim 12, Line 60, delete "reads" and insert -- reads, --, therefor.

In Column 27, Claim 20, Line 15, delete "reads" and insert -- reads, --, therefor.

Signed and Sealed this
Thirtieth Day of July, 2024

Katherine Kelly Vidal
*Director of the United States Patent and Trademark Office*